United States Patent
Niedermeier et al.

(10) Patent No.: US 7,295,317 B2
(45) Date of Patent: Nov. 13, 2007

(54) DEVICE FOR INSPECTING FILLED AND CLOSED RECEPTACLES

(75) Inventors: Anton Niedermeier, Offenstetten (DE); Roland Ederer, Worth/Donau (DE); Rudolf Fiegler, Regensburg (DE)

(73) Assignee: Krones AG., Neutraubling (DE)

( * ) Notice: Subject to any disclaimer, the term of this patent is extended or adjusted under 35 U.S.C. 154(b) by 0 days.

(21) Appl. No.: 10/507,473

(22) PCT Filed: Dec. 10, 2003

(86) PCT No.: PCT/EP03/14062

§ 371 (c)(1), (2), (4) Date: Jul. 11, 2005

(87) PCT Pub. No.: WO2004/053471

PCT Pub. Date: Jun. 24, 2004

(65) Prior Publication Data

US 2005/0248766 A1    Nov. 10, 2005

(30) Foreign Application Priority Data

Dec. 10, 2002   (DE) ............................... 102 57 749

(51) Int. Cl.
*G01N 21/90*    (2006.01)
(52) U.S. Cl. .................... 356/428; 250/223 B
(58) Field of Classification Search ........... 356/428, 356/427; 250/223 B
See application file for complete search history.

(56) References Cited

U.S. PATENT DOCUMENTS

| | | | |
|---|---|---|---|
| 3,811,567 A | 5/1974 | Tomita et al. | |
| 3,900,266 A | 8/1975 | Takahashi et al. | |
| 4,902,137 A * | 2/1990 | Krieg et al. | 356/427 |
| 5,719,679 A | 2/1998 | Shimizu et al. | |
| 5,969,810 A * | 10/1999 | Nicks et al. | 356/239.4 |
| 7,057,718 B2 * | 6/2006 | Kwirandt | 356/239.5 |

FOREIGN PATENT DOCUMENTS

| | | |
|---|---|---|
| DE | 3622000 A1 | 1/1987 |
| DE | 9401926.6 A1 | 3/1994 |
| DE | 4200798 C2 | 8/1994 |
| DE | 4239203 C2 | 12/1995 |
| DE | 10017126 C1 | 6/2001 |
| DE | 10164058 A1 | 7/2002 |
| DE | 101 33 104 A1 | 1/2003 |

(Continued)

*Primary Examiner*—Roy M. Punnoose
(74) *Attorney, Agent, or Firm*—Marshall, Gerstein & Borun LLP

(57) ABSTRACT

A device for inspecting filled and sealed containers consisting of a first carousel in which the containers to be inspected can be rotated about their longitudinal axis so that the contents in the containers begin to rotate with sufficient speed to stir up any foreign bodies that may be present from the bottom of the container and consisting of a second carousel following the first carousel in the direction of transport for bottom-free transport of the containers, at least one inspection device which operates by the dark field method being provided for detection of light scattering foreign bodies in the contents, whereby the two carousels are arranged side by side with their partial circles in tangent so that the containers can be transferred from the first carousel directly to the second carousel.

8 Claims, 2 Drawing Sheets

FOREIGN PATENT DOCUMENTS

| | | |
|---|---|---|
| EP | 726216 | 8/1996 |
| EP | 743267 A1 | 11/1996 |
| EP | 1203946 | 5/2002 |
| JP | 51-20897 A1 | 2/1976 |
| WO | WO 94/08230 | 4/1994 |

* cited by examiner

DEVICE FOR INSPECTING FILLED AND CLOSED RECEPTACLES

FIELD OF THE INVENTION

This invention relates to a device for inspecting filled and sealed containers.

BACKGROUND OF THE INVENTION

WO 94/08230 describes a method and a device for inspecting transparent containers and their liquid contents. The disclosed device has two continuously drivable carousels; the containers that are to be inspected, e.g., filled beverage bottles, pass through these carousels one after the other. In the first carousel as seen in the direction of conveyance, the containers are first rotated once completely about their vertical axis at a low rate of rotation, during which the side wall is observed by a camera for detecting damage or other defects in the container itself. Following this, the rate of rotation is initially increased to induce rotation of the liquid with the goal of creating turbulence to churn up any foreign bodies present on the bottom of the container. Even before leaving the first carousel, the rotational movement of the containers is stopped so they can then be transferred via a first star wheel, a pitch lag screw and a second star wheel to the second carousel, where the containers are inspected by a bright field method and also by a dark field method by cameras that move with the carousels but without any rotation of the containers themselves about their vertical axis in order to detect any foreign bodies in the filling of the containers (suspended materials, particles, etc.).

One disadvantage is that a separate, independently controllable electric motor drive is provided for each container in the first carousel, but this is very high expensive in terms of the drive technology.

Another disadvantage is that the transfer zone from the first carousel to the second turns out to be very long due to the use of the two transfer star wheels with the screw connected in between; this results in a relatively great deceleration of the rotating liquid in the containers even before reaching the second carousel, where the actual foreign body detection in the liquid is then performed. However, the reliability of this inspection method is inadequate at low throughput rates and/or with heavier foreign body particles, in particular transparent bodies, which can be detected reliably only when in movement.

In addition, the conveyance elements mentioned above, which are necessary for the intermediate transfer, depend on the format of the containers to be inspected and must therefore be switched to another type of container with each conversion of the inspection machine [from one product to another]. This is also true of the intake star wheel of the first carousel and the output star wheel of the second carousel. Furthermore, the guide curves arranged between the star wheels are also interchangeable parts that depend on the format.

Because of the great center-to-center distance between the two carousels, the known inspection machine also takes up a relatively large amount of space.

SUMMARY OF THE INVENTION

Based on this prior art, the object of this invention is to provide a device for inspecting filled and sealed containers which will permit a compact design with increased reliability of detection at a lower cost.

Due to the tangent arrangement of the carousels, a direct transfer of the containers from the first carousel to the second carousel without a bypass is possible, which eliminates not only transfer elements that depend on format but also makes it possible for the containers to be inspected immediately for any foreign bodies that might be present in the liquid after rotational acceleration of their liquid contents without any mentionable loss of time, so that even relatively heavy light-scattering foreign bodies can also be detected reliably while in motion before they settle to the bottom of the container even at relatively low throughput rates.

BRIEF DESCRIPTION OF THE DRAWINGS

A preferred exemplary embodiment of this invention is described below on the basis of the figures, which show.

DETAILED DESCRIPTION

Figure 1:
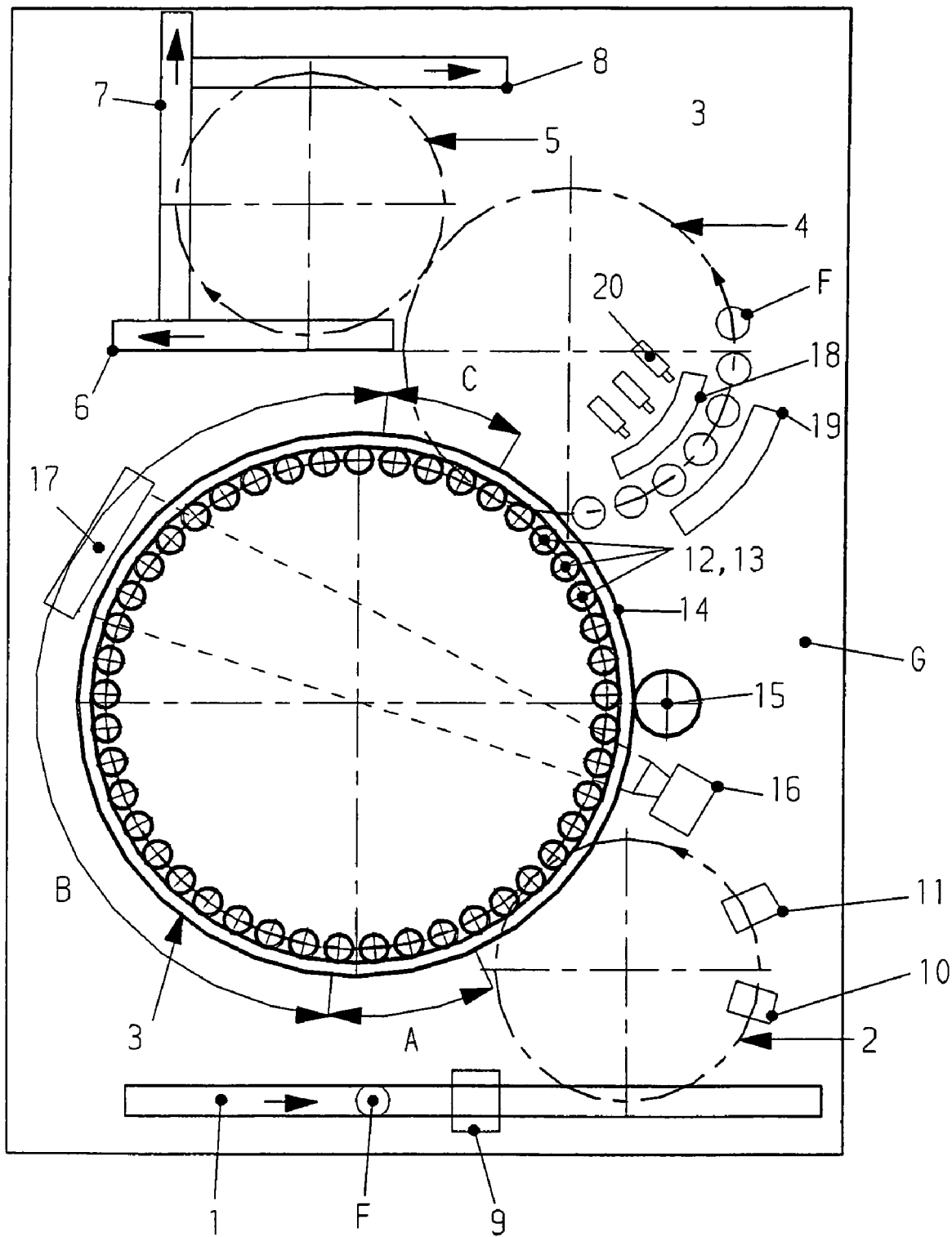
FIG. 1 inspection machine in a highly schematic view from above.

The inspection machine shown schematically in FIG. 1 is set up specially for inspecting filled and sealed beverage bottles made of a transparent or semitransparent material. The bottles F to be inspected are sent continuously from an upstream bottle filling and sealing machine, for example, via a feeder conveyor belt 1 to a feeder star wheel 2, where they pass through a stationary intake inspection station 9 (at the latest before being transferred by the feeder star wheel 2) which checks them for the presence of a seal and may optionally also check the filling level. To prevent soiling of the inspection units due to spillage of liquid from unsealed bottles, such bottles are not gripped by the intake star wheel 2 and they pass by it in the tangential direction in the direction of a downstream collecting point. The same procedure is followed with overfilled or underfilled bottles.

The intake star wheel 2, which can be driven continuously counterclockwise has on its periphery a plurality of selectively controllable gripper clamps arranged at a uniform machine pitch spacing, said grippers being adaptable to different bottle diameters for gripping the bottles in the body area and optionally also in the head and/or neck area. During the transfer from the feeder conveyor belt 1 to a first carousel 3, which follows in the circumferential direction, the bottles are first conveyed forward with a bottom clearance over a stationary bottom blow-off device 10 for removing soap suds or the like and a downstream bottom monitoring station 11 that can be operated by the bright field method for detecting soiling or damage to the bottom of the bottle itself as well as heavy foreign particles that cannot be resuspended by rotating the bottle.

The intake star wheel 2 may be designed, for example, according to European Patent 0 726 216 B1 and European Patent 0 743 267 B1; the bottom blow-off device 10 may be designed according to German Utility Model 94 01 926 U1, and bottom inspection station 11 may be designed according to German Patent Application 101 33 104. The disclosure content of these cited patent applications is explicitly included here.

At the point of contact of the partial circles of the intake star wheel 2 and the first carousel 3 which is revolving counterclockwise, the bottles F with their bottom surfaces are transferred to rotating table 12, which is mounted to rotate about a vertical axis in the carousel, and then the bottles are held in an axial grip so that they can rotate, as is known per se from the prior art which forms the generic type. In the remaining course, the bottles which are upright on the rotating tables 12 are first set in rotation continuously about their vertical axis and accelerated in passing by the first revolving sector A of the carousel 3 and then they pass through the revolving sector B at a defined maximum rotational speed, followed by a revolving sector C for continuous deceleration of the bottle rotation approximately to a standstill.

To create the aforementioned rotational movements of the rotating tables 12, each rotating table has a pinion 13 which is mounted to rotate freely at the bottom on its shaft 22 and meshes with the internal gearing of a toothed gear rim 14 which has internal and external gearing and is supported via a ball bearing slewing rim on the frame plate G of the machine. This toothed gear rim 14 can be driven counterclockwise and in the opposite direction from carousel 3 by a variable speed drive (electric motor or the like) and is controlled by a driving gear wheel 15 that meshes with its exterior gearing. This opposing rotation permits a sufficiently high rotation of the rotating tables. The shafts 22 in passing through the aforementioned revolving sectors A, B, C can be connected more or less greatly to their respective pinion, and in the remaining revolving sector of the carousel 3, they can be connected to the carousel itself via controllable magnetic couplings which are described in greater detail with reference to FIG. 2.

At least one side wall camera 16 is situated on the periphery of the first carousel 3, and diametrically opposite that on the outer side of the carousel 3 there is a side wall luminescent screen 17. This arrangement is used for bright field inspection in transmitted light, which makes it possible to detect damage and/or soiling that causes opacity or opaque suspended particles or the like set in motion by the rotating motion of the liquid in the bottles.

The end area of the rotating sector C of the first carousel 3 is tangent to a second carousel 4 which has—just like the intake star wheel 2—a plurality of selectively controllable grippers for gripping the bottles in the body area and optionally also in the head and/or neck area situated on its periphery and arranged so they are offset with the machine pitch spacing. Thus the bottles F can be gripped at the common point of contact with the first carousel 3 and transferred with a bottom clearance counterclockwise in the direction of the following sorting star wheel 5, whereby on the way there the bottles are subjected to a foreign body detection in the dark field method with which light-scattering foreign bodies, in particular transparent splinters of glass, can be detected.

To this end, equidistant luminescent screens 18 and 19 which are adapted to the curvature of the path are arranged in stationary positions on both sides of the curved peripheral :path of the bottles F, so that the bottles can pass freely between the screens and be illuminated over the largest possible area from the sides. Due to the simultaneous bilateral tunnel-like illumination, a very high light induction into the bottles can be achieved, which is advantageous in particular in the case of opaque or dark liquids such as beer-containing yeast or colas. Luminescent screens 18 and 19 may preferably be equipped with a plurality of LEDs which can be operated in a pulsating manner by a lighting control device.

Furthermore, the second carousel 4 is equipped with cameras 20 arranged beneath its grippers (not shown), e.g., one camera per gripper whereby the cameras revolve in positional synchronization with the grippers and are able to image the bottom of the illuminated bottles, optionally using deflector mirrors (not shown here) positioned beneath the bottles at an oblique angle. This arrangement achieves a dark field lighting in which the light scattering defects and/or foreign bodies appear as light spots or zones in an otherwise dark image.

Alternatively, a stationary arrangement of one or more cameras would also be conceivable. By simultaneous triggering of the cameras 20 to record the image and the LEDs of the luminescent screens 18 and 19, the triggering that would otherwise be necessary may be omitted. Furthermore, a modification in which one camera can always detect and image several bottle bottoms simultaneously through a suitable mirror arrangement is also possible.

The sorting star wheel 5 which is also equipped with selectively controllable grippers (not shown) is capable of delivering the inspected bottles to various conveyor belts as a function of the test results by bottom inspection station 11 side wall camera 16 and cameras 20 which observe the bottles F through the bottom. Thus, for example, the bottles without a distance between them may leave the inspection machine via the discharge conveyor belt labeled as 6 while bottles having defects can be diverted to either discharge belts 7 or 8, depending on the type of defect detected.

Figure 2:
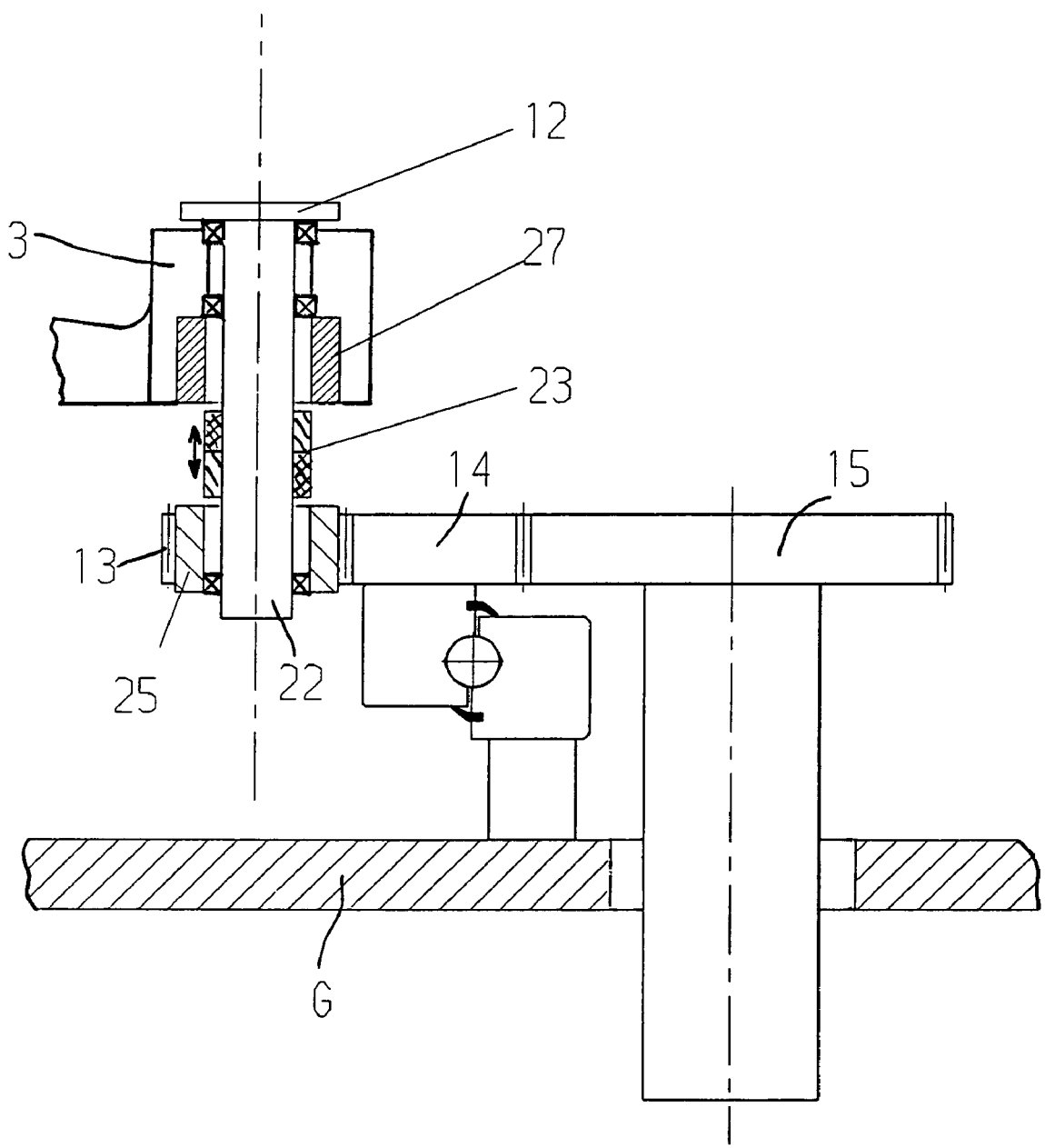
FIG. 2 a vertical partial section through the outer peripheral area of a first carousel of the inspection machine in FIG. 1.

FIG. 2 shows in detail the drive for the rotating tables 12 arranged on the first carousel 3. The rotating tables 12 are each arranged fixedly on the upper end of shafts 22 mounted vertically in carousel 3_so they can rotate on a common partial circle. On each shaft 22, a magnetic ring 23 is guided so that it is axially displaceable up and down and engages in a rotationally fixed manner with its shaft 22 for transmission of torque. Furthermore, a hysteresis ring 27 is arranged in a rotationally fixed manner, coaxially with each shaft 22 in the carousel 3, the inside diameter of this hysteresis ring being slightly larger than the outside diameter of the magnetic ring 23. A second hysteresis ring 25 having an inside diameter which slightly exceeds the outside diameter of the magnetic ring 23 is mounted on the shaft 22 so that it is coaxial and freely rotatable; it is arranged with an axial distance beneath the aforementioned first hysteresis ring 27 so that it is rotationally fixed with each pinion 13, which engages with the toothed rim 14. The axial distance between the two hysteresis rings 25 and 27 corresponds approximately to the height of the magnetic ring 23 which is equipped with several oppositely polarized permanent magnets arranged in alternation on the circumference, at least on its upper and lower edges. The hysteresis rings are made of a material having a high permeability such as soft iron.

Each of the magnetic rings 23 is movable up and down longitudinally along the shaft 22 by means of an activating device not shown here, e.g., a mechanical cam control and can thus form a magnetic coupling optionally with: the drivable lower hysteresis ring 25 or the upper rotationally fixed hysteresis ring 27, whereby the transmittable torque is variable via the depth of immersion, i.e., the axial coverage of the magnetic ring 23 with the respective hysteresis ring. The controllable coverage permits a simple means of controlling the acceleration torque and/or the braking torque which can be transmitted to a bottle F in the individual peripheral sectors of the carousel 3. In this way, each rotating table 12 can be acted upon by torque with an accelerating or decelerating effect with practically no wear during a revolution with the carousel in the correct position for the instantaneous rotational position without any electrotechnical complexity and independently of the neighboring rotating tables.

Therefore, individual electric motor drives are not necessary for each rotating table. The drive for all rotating tables 12 may be derived easily via the toothed rim 14 and the driving gear wheel 15 from the central machine drive alone, so that synchronization of speed and rotational position is automatically ensured for all the remaining process sequences of the inspection machine.

In deviation from this, however, a separate variable-speed motor drive independent of the machine drive may also be used, acting upon drive wheel 15.

The invention claimed is:

1. A device for inspecting filled and sealed containers, the device comprising: a first carousel comprising driving elements for rotating containers about their longitudinal axes such that the containers to be inspected can be rotated about their longitudinal axis so that the contents in the containers begin to rotate at a sufficient speed to cause any foreign bodies that might be present to be stirred up from the bottom of the containers, and a second carousel which follows the first carousel in the direction of conveyance for conveying containers with a bottom clearance, the second carousel being assigned at least one inspection device that operates by the dark field method for detecting light scattering foreign bodies in the container contents, and the first and second carousels are arranged side by side with their partial circles tangent so that the containers can be transferred directly from the first carousel to the second carousel.

2. The device according to claim 1, further comprising a star wheel which transports the containers with a bottom clearance and is arranged upstream from the first carousel as seen in the direction of transport and is assigned one of at least one bottom blow-off device and a bottom inspection station that operates by the bright field method.

3. The device according to claim 1, further comprising an intake inspection for one of checking the filling levels and the container closures, the intake inspection provided one of upstream from the star wheel and the first carousel.

4. The device according to claim 3, wherein unsealed containers are not transferred from the star wheel or the first carousel.

5. The device according to claim 1, wherein the first carousel has multiple drivable rotating tables on a partial circle, said tables being engageable or disengageable in a frictionally locked manner via controllable magnetic couplings with a drive element of the driving elements that all the rotating tables have in common.

6. The device according to claim 5, wherein the magnetic couplings are hysteresis clutches with a variable torque.

7. The device according to claim 1, further comprising luminescent screens that are diametrically opposed and are adapted to the curvature of the path so they are equidistant, the luminescent screens provided in at least some sections on both sides of the peripheral path of the second carousel and simultaneously lighting up the containers laterally at the same time while the bottom is being photographed.

8. The device according to claim 7, wherein the luminescent screens are equipped with LEDs that can be triggered in a pulsating pattern and are always triggerable simultaneously with a photograph of the bottom.

* * * * *

UNITED STATES PATENT AND TRADEMARK OFFICE
CERTIFICATE OF CORRECTION

PATENT NO.       : 7,295,317 B2
APPLICATION NO.  : 10/507473
DATED            : November 13, 2007
INVENTOR(S)      : Anton Niedermeier et al.

It is certified that error appears in the above-identified patent and that said Letters Patent is hereby corrected as shown below:

On the Title Page:

item (73), "Krones AG." should be -- Krones AG --.

item (30), "102 57 749" should be -- 102 57 749.8 --.

Signed and Sealed this

Seventeenth Day of June, 2008

JON W. DUDAS
*Director of the United States Patent and Trademark Office*